United States Patent
Scott (10) Patent No.: US 7,407,625 B1
(45) Date of Patent: Aug. 5, 2008

(54) VOLUME-DIFFERENTIAL WATER ASSAY SYSTEM USING HYDROPHILIC GEL

(75) Inventor: Bentley N. Scott, Garland, TX (US)

(73) Assignee: Phase Dynamics, Inc., Richardson, TX (US)

( * ) Notice: Subject to any disclaimer, the term of this patent is extended or adjusted under 35 U.S.C. 154(b) by 0 days.

(21) Appl. No.: 11/106,356

(22) Filed: Apr. 14, 2005

Related U.S. Application Data (60) Provisional application No. 60/565,981, filed on Apr. 28, 2004.

(51) Int. Cl.
*G01N 33/18* (2006.01)
*G01N 21/05* (2006.01)
*G01N 1/10* (2006.01)
*B01L 3/00* (2006.01)

(52) U.S. Cl. .............. 422/59; 73/61.43; 73/61.59; 73/73; 73/76; 422/61; 422/69; 422/101; 436/39; 436/40; 436/178

(58) Field of Classification Search .......... 73/61.43, 73/61.59, 73, 76; 422/59–61, 69, 72, 99–102; 436/39–40, 45, 167, 177–178
See application file for complete search history.

(56) References Cited

U.S. PATENT DOCUMENTS

| | | | | |
|---|---|---|---|---|
| 270,489 A | * | 1/1883 | Schubert | 73/61.65 |
| 2,110,237 A | * | 3/1938 | Parsons | 73/61.71 |
| 2,760,368 A | * | 8/1956 | Coffman | 73/61.43 |
| 3,528,775 A | * | 9/1970 | O'Hara et al. | 436/40 |
| 3,712,118 A | * | 1/1973 | Mason et al. | 73/61.59 |
| 3,733,179 A | * | 5/1973 | Guehler | 436/71 |
| 3,745,659 A | * | 7/1973 | Hsu | 33/720 |
| 3,873,271 A | * | 3/1975 | Young et al. | 436/40 |
| 3,885,921 A | * | 5/1975 | Matsumoto et al. | 23/300 |
| 3,970,429 A | * | 7/1976 | Updike | 436/535 |
| 3,976,572 A | * | 8/1976 | Reick | 210/94 |
| 4,004,453 A | * | 1/1977 | Thyrum | 73/61.59 |
| 4,055,986 A | * | 11/1977 | Stewart et al. | 73/61.72 |
| 4,257,775 A | * | 3/1981 | Ladov et al. | 436/40 |
| 4,557,899 A | * | 12/1985 | Schoonover et al. | 422/55 |
| 4,587,284 A | * | 5/1986 | Luissi et al. | 524/17 |
| 4,655,076 A | * | 4/1987 | Weihe et al. | 73/73 |
| 4,861,469 A | * | 8/1989 | Rossi et al. | 210/172 |
| 5,146,778 A | * | 9/1992 | Hsu | 73/61.41 |

(Continued)

OTHER PUBLICATIONS

Mehdizadeh, P; Marrelli, J; Ting, V.C.; Wet Gas Metering: Trends in Applications and Technical Developments, SPE 77351 (SPE Annual Technical Conference and Exhibition in San Antonio, Texas Sep. 29-Oct. 2, 2002); pp. 1-14, Society of Petroleum Engineers Inc.; Richardson, Texas, USA.

*Primary Examiner*—Arlen Soderquist
(74) *Attorney, Agent, or Firm*—Groover & Associates (57) ABSTRACT

Systems and methods for measuring the moisture and sediment content of a petroleum sample. In one embodiment, a sample to be tested is collected in a field bottle. The sample from the field bottle is then transferred from the field bottle, and into and through a measurement column containing a high-uptake gelling agent, such as a superabsorbent polymer. The sample's moisture is determined by measuring the expanded volume of the high-uptake gelling agent. The measurement column also contains a sediment measurement section having a sediment filter and a sight glass with graduations to measure the sediment content of the sample.

24 Claims, 8 Drawing Sheets

U.S. PATENT DOCUMENTS

| | | | |
|---|---|---|---|
| 5,308,771 A | * | 5/1994 | Zhou et al. .................... 436/39 |
| 5,603,955 A | * | 2/1997 | Gehrke et al. ............... 424/484 |
| 5,694,806 A | * | 12/1997 | Martin et al. .................. 73/73 |
| 6,387,325 B1 | * | 5/2002 | Keusch et al. ................. 422/50 |
| 6,593,753 B2 | | 7/2003 | Scott et al. |
| 6,810,719 B2 | | 11/2004 | Dutton et al. |

* cited by examiner

VOLUME-DIFFERENTIAL WATER ASSAY SYSTEM USING HYDROPHILIC GEL

CROSS-REFERENCE TO RELATED APPLICATIONS

This application claims priority from U.S. Provisional Application 60/565,981 filed 28 Apr. 2004, which is hereby incorporated by reference.

BACKGROUND AND SUMMARY OF THE INVENTION

The present inventions relate generally to a laboratory or portable measurement method and system, and more particularly, to a method and system for the point of sale measurement of the water and sediment content in a petroleum sample.

Conventional Methods for Measuring Water Content

A determination of water content in crude oil is required to measure accurately net volumes of actual oil in sales, taxation, exchanges, and custody transfers. The water content of crude oil is also significant because it can cause corrosion of equipment and problems in processing. Thus, various methods have been developed for measuring the water content of crude oil.

Karl Fischer Titration Method

In 1935, German scientist, Karl Fischer, developed a titrimetric determination of water content using a reagent that contained iodine, sulphur dioxide, anhydrous pyridine, and anhydrous methanol. This method can be subdivided into two main techniques: volumetric titration and coulometric titration.

The volumetric technique involves dissolving the sample in a suitable solvent and adding measured quantities of a reagent containing iodine until an end point is reached. This end point is determined potentiometrically using a platinum electrode. When all of the water has reacted, the platinum measuring indicator electrode will electronically instruct the burette to stop dispensing. The volume of KF reagent dispensed is recorded. Based on the concentration of iodine in the KF reagent, the amount of water present is then calculated.

However, even with the automatic or semi-automatic instruments commercially available, there are certain problems associated with this technique. These problems include long analysis time, required reagent calibration, and high reagent consumption rate.

In the coulometric technique developed by Meyer and Boyd in 1959, the sample is introduced into a mixture of pyridine/methanol that contains iodide ions and sulphur dioxide. The electrode system consists of an anode and cathode platinum electrodes that conduct electricity through the cell. Iodine is generated at the anode and reacts with any water present. The production of iodine is directly proportional to the amount of electricity according to Faraday's Law as shown in the equation:

$$2I^- - 2e \rightarrow I_2.$$

According to the stoichiometry of the reaction, 1 mole of iodine will react with 1 mole of water, and combining this with coulometry, 1 milligram of water is equivalent to 10.71 coulombs of electricity. Therefore, it is possible to directly determine the amount of water present in a sample by measuring the electrolysis current in coulombs. The platinum indicating electrode voltametrically senses the presence of water and continues to generate iodine until all the water in the sample has been reacted.

From this titration, the onboard microprocessor calculates the total amount of current consumed in completing the titration and the time to completion in seconds. Based on the relationship between coulombs and iodine, the exact amount of iodine generated is recorded. Since water reacts in the 1:1 ratio with iodine, the amount of water can be calculated.

Although the original Karl Fischer reagent contained pyridine, most reagent manufacturers now use other amines such as imidazol.

Karl Fischer titration is one of the most widely used techniques for measuring the water content in a large range of samples. However, it has limits that affect its usefulness. For example, it utilizes hazardous reagents that require the operator to exercise care in the storing, handling, and disposing of reagents that degrade with time. With the techniques, a total sample size of 0.5 ml. or smaller is taken from a larger sample size, typically 250 ml. The small sample size utilized by the techniques causes errors and cannot measure water percentages over 1% accurately. Also, the Karl Fischer titration techniques are operator intensive and do not provide any information with regard to the amount of sedimentation in a sample.

(Please see *Manual of Petroleum Measurement Standards*, Chapter 10.7—*Standard Test Method for Water in Crude Oils by Potentiometric Karl Fischer Titration* and Chapter 10.9—*Determination of Water in Crude Oils Coulometric Karl Fischer Titration* for the complete protocols, which are hereby incorporated by reference.)

Centrifuge Method

In the standard method for determining the water content in crude oil by centrifuge, equal volumes of a sample and water saturated toluene are placed into two cone-shaped centrifuge tubes. The tubes are then corked and placed into a centrifuge. The tubes are then spun, for example, for 10 minutes at a minimum relative centrifugal force of 600 calculated from the following equation:

$$rmp = 1335\sqrt{rcf/d}$$

where:

rcf=relative centrifugal force and d=diameter of swing measured between tips of opposite tubes when in rotating position, mm.

Immediately after the centrifuge comes to rest following the spin, the combined volume of water and sediment at the bottom of each tube is read and recorded. The spin is then repeated until the combined volume of water and sediment remains constant for two consecutive spins. The final volume of water is then recorded for each tube.

The standard method for determining the water content by centrifuge is not entirely satisfactory. The amount of water detected is almost always lower than the actual water content. Therefore, when a high accurate value is required, another method must be used. This method also requires hazardous solvents and has very poor accuracy and reproducibility.

(Please see *Manual of Petroleum Measurement Standards*, Chapter 10.3—*Standard Test Method for Water and Sediment in Crude Oil by the Centrifuge Method* (*Laboratory Procedure*) for the complete protocol, which is hereby incorporated by reference.)

Distillation Method

In the standard test for determining the water content by distillation, the sample is heated under reflux conditions with a water immiscible solvent that co-distills with the water in the sample. The condensed solvent and water are continuously separated in a trap wherein the water settles in the graduated section of the trap, and the solvent returns to the distillation flask. The amount of water can then be determined on a volume or a mass basis.

The precision of this method can be affected by water droplets adhering to surfaces in the apparatus and, therefore, not settling into the water trap to be measured. To minimize this problem, all apparatus must be chemically cleaned at least daily to remove surface films and debris that hinder the free drainage of water in the apparatus.

If the system forms azeotropes, as in a benzene and cyclohexane system, a different problem arises, —the azeotropic composition limits the separation, and for a better separation, this azeotrope must be bypassed in some way. At low to moderate pressure, with the assumption of ideal-gas model for the vapor phase, the vapor-liquid phase equilibrium (VLE) of many mixtures can be adequately described by the following Modified Raoult's Law:

$$y_i P = x_i \gamma_i P_i^{sat} \text{ for } i=1, \ldots, c$$

where
$y_i$=mole fraction of component i in vapor phase;
$x_i$=mole fraction of component i in liquid phase;
P=system pressure;
$P^{sat}$=vapor pressure of component i; and
$\gamma_i$=liquid-phase activity coefficient of component i.

When $\gamma_i$=1, the mixture is said to be ideal, and the equation simplifies to Raoult's Law. Nonideal mixtures ($\gamma_i \neq 1$) can exhibit either positive ($\gamma_i > 1$) or negative deviations ($\gamma_i < 1$) from Raoult's Law. In many highly nonideal mixtures, these deviations become so large that the pressure-composition (P-x, y) and temperature-composition (T-x, y) phase diagrams exhibit a minimum or maximum azeotrope point. In the context of the T-x, y phase diagram, these points are called the minimum boiling azeotrope (where the boiling temperature of the azeotrope is less than that of the pure component) or maximum boiling azeotrope (the boiling temperature of the azeotrope is higher than that of the pure components). About 90% of the known azeotropes are of the minimum variety. At these minimum and maximum boiling azeotrope, the liquid phase and its equilibrium vapor phase have the same composition, i.e.:

$$x_i = y_i \text{ for } i=1, \ldots, c \qquad (2)$$

Two main types of azeotropes exist, i.e. the homogeneous azeotrope, where a single liquid phase is in the equilibrium with a vapor phase; and the heterogeneous azeotropes, where the overall liquid composition, which forms two liquid phases, is identical to the vapor composition. Most methods of distilling azeotropes and low relative volatility mixtures rely on the addition of specially chosen chemicals to facilitate the separation.

The drawbacks to this method include, for example, the fact that it utilizes hazardous solvents and produces hazardous vapors. This method also takes 2 to 3 hours to complete, and as with most distillation techniques, the accuracy and precision of the results will depend upon the skill of the technician performing the distillation. This method also does not provide any information with regard to the amount of sedimentation in the sample.

(Please see *Manual of Petroleum Measurement Standards*, Chapter 10.2—*Standard Test Method for Water in Crude Oil Distillation* for the complete protocol, which is hereby incorporated by reference.)

Superabsorbent Polymers

Superabsorbent polymers are materials that have the ability to absorb and retain large volumes of water and aqueous solutions. This makes them ideal for use in water absorbing applications such as baby nappies, absorbent medical dressings, and controlled release mediums.

Early superabsorbents were made from chemically modified starch and cellulose and other polymers like poly(vinyl alcohol) PVA, poly(ethylene oxide) PEO, all of which are hydrophilic and have a high affinity for water. When lightly cross-linked, chemically or physically, these polymers became water-swellable but not water-soluble.

Today's superabsorbent polymers are made from partially neutralized, lightly cross-linked poly(acrylic acid), which has been proven to give the best performance versus cost ratio. The polymers are manufactured at low solids levels for both quality and economic reasons, and are dried and milled in to granular white solids. In water, they swell to a rubbery gel that in some cases can be up to 99% water by weight.

The driving forces behind a superabsorbent polymer's water absorbency are osmotic pressure and hydrogen bonding. The difference in the sodium ion concentration between the inside of the polymer and the solution in which it is immersed causes the water to flow in rapidly, trying to balance the number of ions inside and outside the polymer. Also, the polymer chains are lined with carboxyl groups (—COOH) with about 50 to 70% of these in the sodium salt form. In contact with water, the carboxyl groups dissociate into negatively charged carboxylate ions (—COO—). These form hydrogen bonds with water molecules.

In addition, these carboxylate sites repel each other. This repulsion widens the polymer network, thus allowing more water to be absorbed. However, the crosslinked polymer molecules can only stretch so far. Therefore, the amount of water absorbed is in part determined by the balance between widening of the polymer network as hydrogen bonds form and "elastic pressure" of the crosslinked molecules.

The electrolyte concentration in the water being absorbed greatly affects the amount of fluid that can be absorbed by the polymer. The ions of the electrolyte act as "contaminator" ions and become positioned along the polymer chain at the carboxylate sites. The electrolyte ions partially neutralize these sites and limit the potential sites for hydrogen bond formation between the polymer and water molecules. In addition, there will be less repulsion between the crosslinked chains of the polymer, thus enabling less water to be absorbed. Also, the presence of these ions decreases the unbalance that "drives" osmotic pressure.

A typical superabsorbent polymer may absorb about 400 times its own mass of distilled water while absorbing almost 300 times its mass of tap water. The same polymer may absorb only 30 to 40 times its mass of 1% sodium chloride solution.

Volume-Differential Assay Using Hydrophilic Gel

The present inventions describe systems and methods for the determination of the water and sediment content in a petroleum sample.

The present innovations include, in one embodiment, collecting a sample to be tested in a field bottle. The sample from the field bottle is then transferred from the field bottle, and into and through a measurement column containing a high-uptake gelling agent, such as a superabsorbent polymer. The sample's moisture can be determined by measuring the expanded volume of the high-uptake gelling agent inside the measurement column. The measurement column also contains a sediment measurement section having a sediment filter and a sight glass with graduations to measure the sediment content of the sample.

Hence, the disclosed innovations provide a simple approach to measuring the moisture and sediment content in crude oil that is extremely fast, accurate, and reproducible without the use of hazardous chemicals. Other embodiments are described more fully below.

BRIEF DESCRIPTION OF THE DRAWINGS

The disclosed inventions will be described with reference to the accompanying drawings, which show important sample embodiments of the invention and which are incorporated in the specification hereof by reference, wherein.

DETAILED DESCRIPTION OF THE PREFERRED EMBODIMENTS

The numerous innovative teachings of the present application will be described with particular reference to the presently preferred embodiment (by way of example, and not of limitation).

Figure 1:
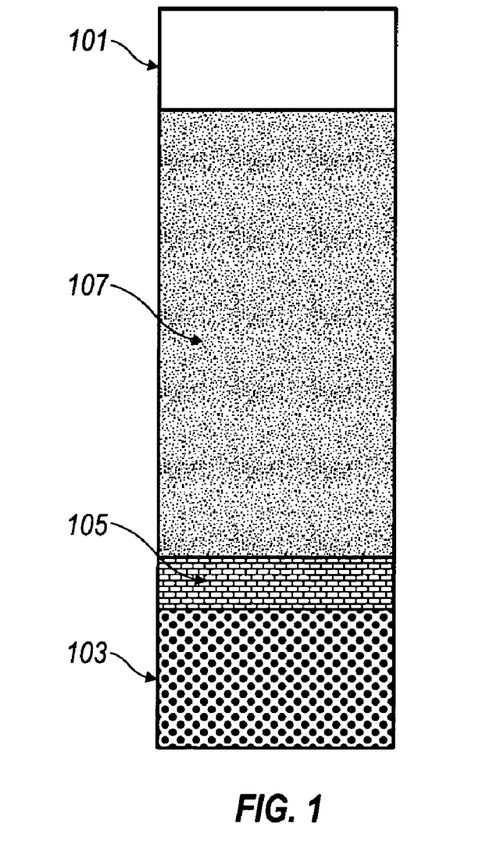
FIG. 1 shows an embodiment of the present inventions using a tube system and hydrophilic membrane.

FIG. 1 shows a preferred embodiment of the present inventions using a tube system and hydrophilic membrane. In this particular embodiment, tube 101 is prepared with an adequate amount of high-uptake gelling agent 103. Tube 101 can be any type of graduated tube, such as a test tube or a centrifuge tube. A hydrophilic membrane 105 is placed on top of gelling agent 103. Hydrophilic membrane 105 can be comprised of any material that can absorb and transfer moisture from an area having a relatively higher moisture concentration to an area having a relatively lower moisture concentration. An oil sample 107 is obtained and poured into tube 101. Tube 101 is then capped and shaken. This allows the water content in oil sample 107 to be adsorbed by membrane 105 and then absorbed by gelling agent 103. As gelling agent 103 absorbs water from oil sample 107, gelling agent 103 expands, moving membrane 105 up tube 101. The total volume of the expanded gel is then measured, using membrane 105 as a marker, to determine the amount of water absorbed from oil sample 107.

Although this particular embodiment shows a membrane as a marker, any substance that allows the top of the expanded gelling agent to be more discernible can be used. For example, cobalt chloride, which is an anhydrous salt that changes from a blue color to a pink color in the presence of moisture, can be used. Florescent dyes, such as flourescene, may also be used as a marker.

Figure 2:
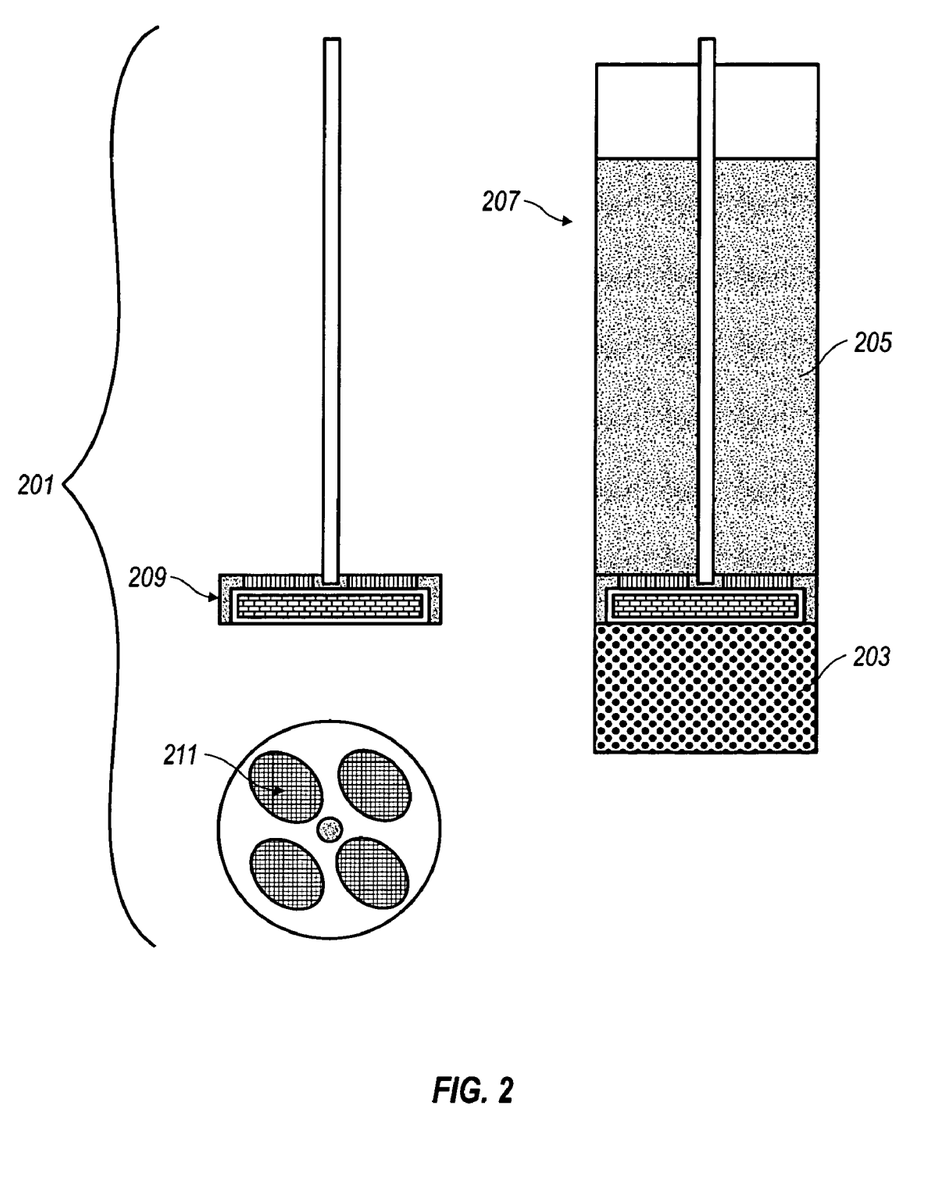
FIG. 2 shows a plunger assembly used with a tube system to filter out the gel from the fluid sample.

FIG. 2 shows a plunger assembly used with a tube system to filter out the absorbent gel from a fluid sample. In this particular embodiment, a plunger assembly 201 is used to filter out the absorbent gel 203 from the fluid sample 205 and compress it to the bottom of a tube 207. This allows the total gel volume to be measured more accurately. Plunger assembly 201 is shown with a plunger cup 209. Plunger cup 209 is fitted to seal against the inner wall of tube 207. Plunger cup 209 utilizes a mesh 211 with a mesh size small enough to prevent absorbent gel from passing through with the rest of fluid sample 205.

In another preferred embodiment, the present innovations involve obtaining a sample of petroleum for moisture and sediment determination in a field bottle, and placing the sample-filled field bottle in an apparatus that allows the sample to flow from the field bottle and into a measurement column containing a high-uptake gelling agent. The sample then flows through the measurement column and into a receiving bottle. The sample's moisture is determined by measuring the expanded volume of the high-uptake gelling agent inside the measurement column. The measurement column also contains a sediment measurement section having a sediment filter and a sight glass with graduations to measure the sediment content of the sample.

Figure 3:
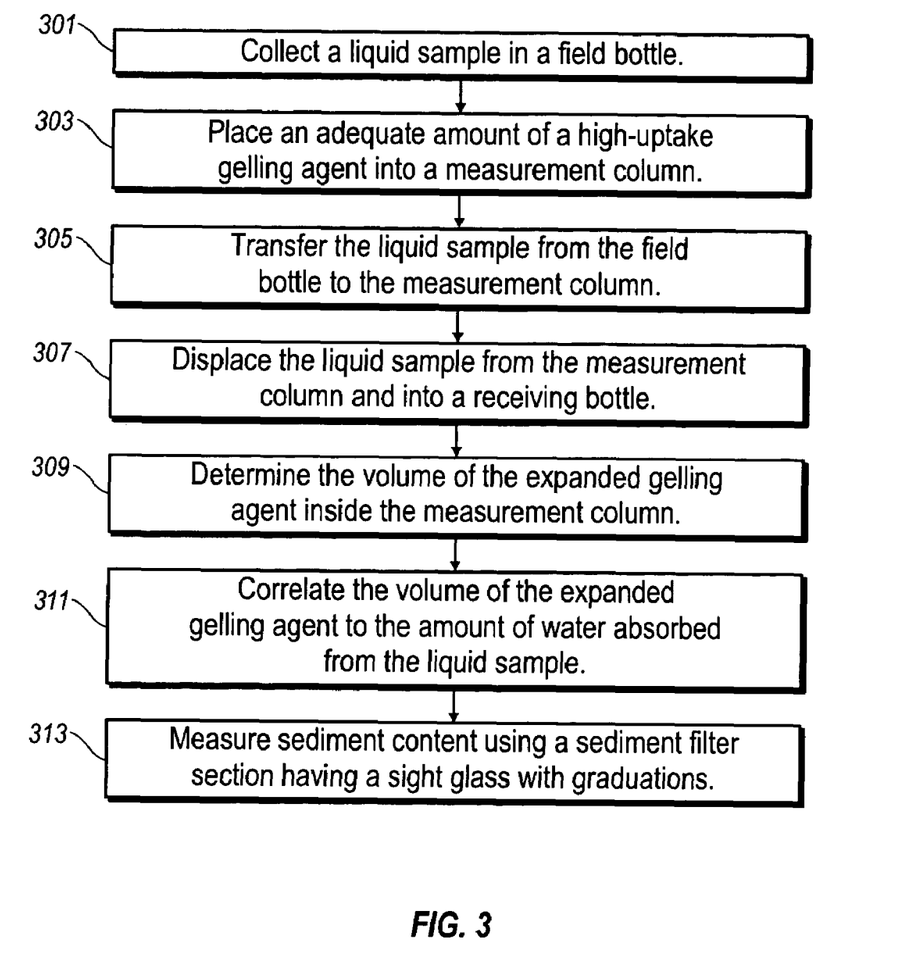
FIG. 3 is a flow chart of a preferred embodiment of the present inventions.

FIG. 3 is a flow chart of a preferred embodiment of the present inventions. In this embodiment, a fluid sample is collected in a field bottle (step 301). An adequate amount of a high-uptake gelling agent is placed into a measurement column (step 303). The amount of gelling agent used is an amount such that the gelling agent does not become saturated by the amount of moisture absorbed from the sample. The sample is then transferred from the field bottle and into and through the measurement column (step 305). The fluid sample is displaced from the measurement column and into a receiving bottle (step 307). The total volume of the expanded gelling agent inside the measurement column is then determined (step 309). The total volume of the expanded gelling agent is then correlated to the amount of moisture absorbed from the sample (step 311). A sediment measurement section having a sediment filter and a sight glass with graduations can be used to measure the sediment content of the sample (step 313). The sediment measurement section is placed before the gelling agent section such that the sediment can be measured separately from the water content.

Some gelling agents, such as polyacrylic acid, expand in a 1:1 ratio with the amount of moisture absorbed. Therefore, the amount of moisture absorbed can be determined directly by measuring the total volume of the expanded gelling agent. Although polyacrylic acid and other gelling agents having a 1:1 expansion ratio with the volume of moisture absorbed is a preferred embodiment, any gelling agent with a known ratio of total expanded volume to volume of moisture absorbed can be used.

Any inert solid, such as glass beads, that will aid in adding occlusions may be added to the gelling agent to make the gelling agent more permeable by forming occlusion areas. This would allow the fluid sample to pass through the gelling agent more readily by preventing the gelling agent from occluding the passage of the sample fluid.

As with the previous embodiment, any substance that allows the top of the expanded gelling agent to be more discernible also can be used with this embodiment.

Figure 4:
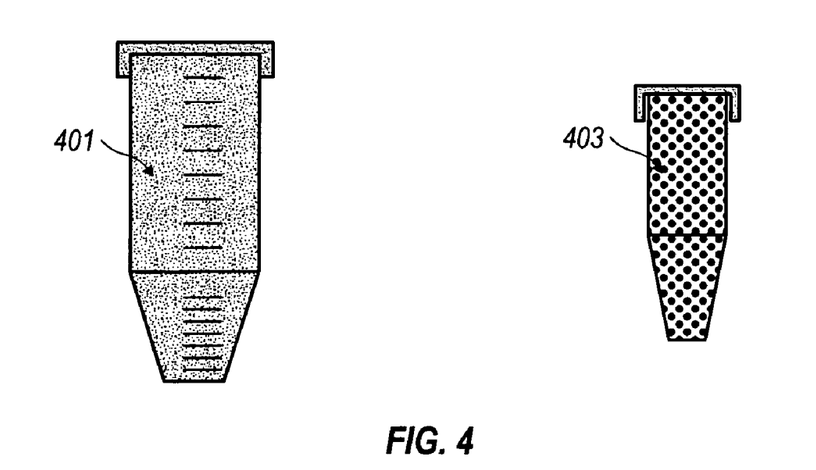
FIG. 4 shows a field bottle and a receiver bottle.

FIG. 4 shows a sample embodiment of a field bottle 401 and a receiver bottle 403. Both bottles can be standard plastic centrifuge tubes such as Cole-Palmer A-06334-40 and A-17410-20 with lids. In this particular embodiment, field bottle 401 is a 250 ml. container used by field personnel to pull a sample from a crude oil pipeline. Receiver bottle 403 is a 10 ml. tube or insulated container used to collect the sample once it has passed through the measurement column.

Figure 5:
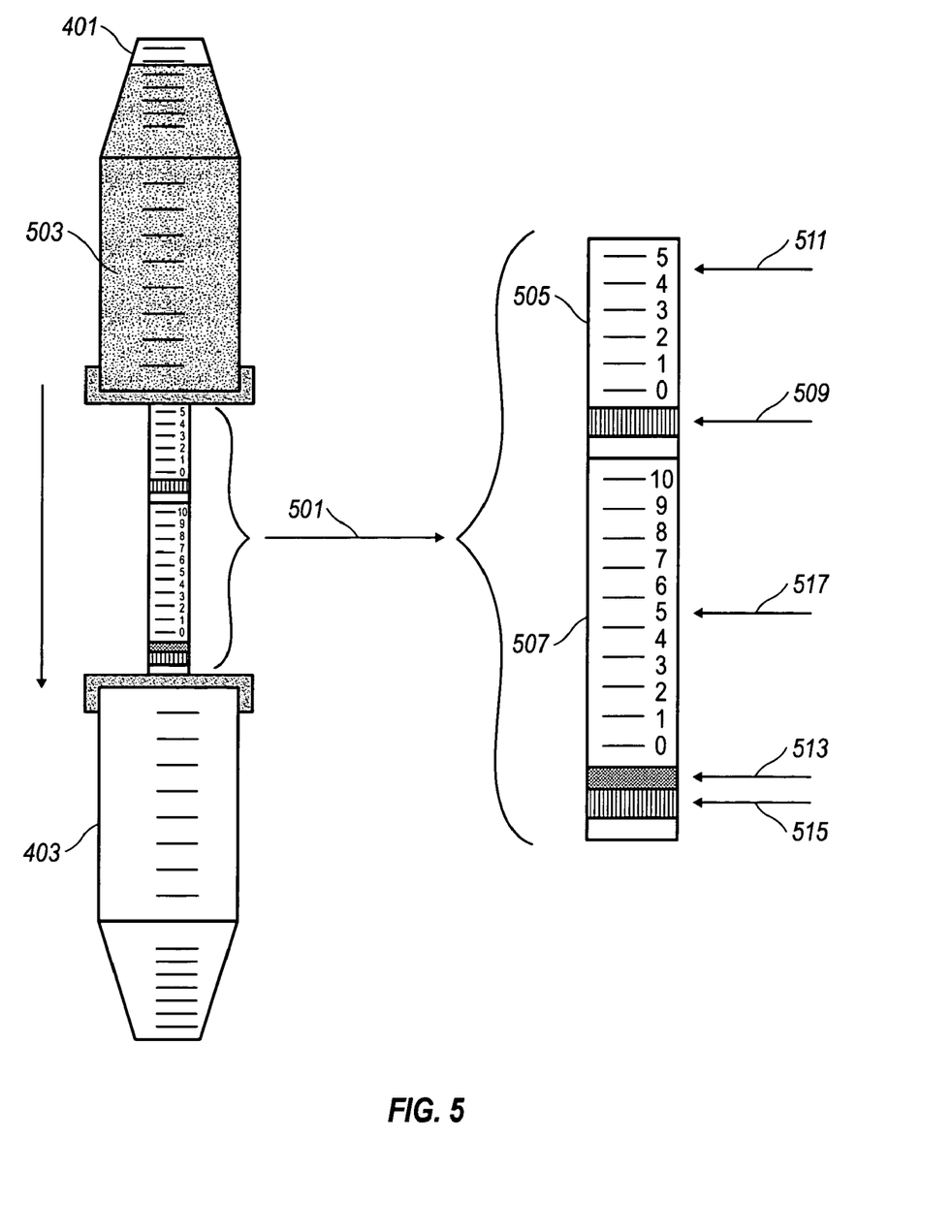
FIG. 5 shows a general layout of a sample embodiment of a basic gravity type system.

FIG. 5 shows a general layout of a sample embodiment of a basic gravity type system. In this particular embodiment, a fluid sample 503 is transferred from field bottle 401 to measurement column 501. Measurement column 501 is fitted with a sediment measurement section 505 and a moisture measurement section 507. Sediment measurement section 505 comprises a filter 509 that retains sediments while allowing the rest of fluid sample 503 to flow into moisture measurement section 507. Sediment measurement section 505 also comprises a sight glass tube 511 with graduations to measure the sediment content of fluid sample 503. Moisture measurement section 507 comprises an adequate amount of gelling agent 513 along with a filter 515 to retain gelling agent 513 while allowing fluid sample 503 to flow through moisture measurement section 507 and into receiver bottle 403. Gelling agent 513 also contains a marker, such as an anhydrous salt, a florescent dye, a membrane, or other marker that allows the top of the expanded gelling agent to be more discernible. Moisture measurement section 507 also comprises a sight glass tube 517 with graduations to measure the volume of expanded gelling agent 513.

Measurement column 501 is replaceable to avoid contamination of the next sample, as well as minimizes disposal. As with the previous embodiments, any inert solid, such as glass beads, that will aid in adding occlusions may be added to the gelling agent to make the gelling agent more permeable by forming occlusion areas. This would allow the fluid sample to pass through the gelling agent more readily by preventing the gelling agent from occluding the passage of the sample fluid.

Another embodiment of the present innovations can be implemented by adding a gelling agent directly to the fluid sample and thoroughly mixing the combination prior to centrifuge.

As noted earlier, the standard centrifuge method for determining the water content of crude oil is to dilute the sample with an equal amount of water saturated toluene as a solvent. The sample is then heated and centrifuged.

Problems associated with the standard centrifuge method include the use of solvents, handling of the sample, and reading the meniscus on the graduated centrifuge tube. The oil also will be held up by the crude because of the surface tension surrounding the water droplet. This causes the results of the water content always to be lower than the actual water content of the sample. Although heating and diluting the crude with solvents helps with this problem, the solvent still needs to be water saturated so as not to affect the measurement.

The present inventions provide a solution to many of these problems by adding a gelling agent to the crude oil and thoroughly shaking the mixture before centrifuge. Using a gelling agent would eliminate the need for the solvent and heat except for high viscosity (almost solid) samples. The gelling agent will collect and gel the water thereby allowing the water to be removed and separated from the crude oil during centrifuge. This would potentially eliminate the need for hazardous solvents and remove all of the water from the crude oil thereby improving the measurement. Since no hazardous chemicals were added, the fluids can be placed back into the crude oil processing line instead of removal to a hazardous chemical site. The line between the oil and water formed by the centrifuge step would be more easily discernible because the water would be gel-like.

Figure 6A:
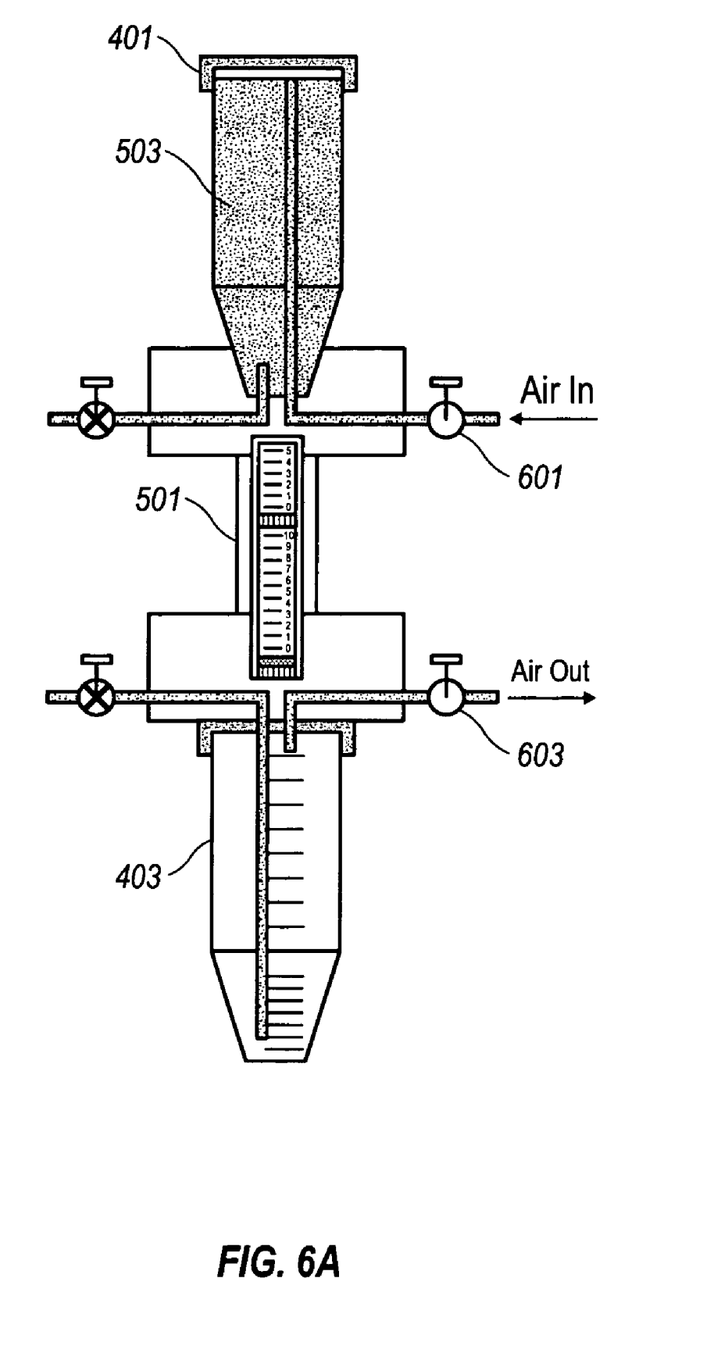
FIGS. 6A-6C show a general layout of sample embodiments that utilize a valve system.

FIG. 6A shows a general layout of a sample embodiment that utilizes a valve system to allow air to enter the field bottle. Valve 601 is opened to displace fluid sample 503 from field bottle 401 by allowing air to enter field bottle 401. In this particular embodiment, gravity is used to pull fluid sample 503 through measurement column 501. Once fluid sample 503 has passed from field bottle 401 and through measurement column 501, valve 603 is used to release air from the top of receiver bottle 403. By having separate tubes to each bottle (one to the bottom of the bottles and one to the top of the bottles), the top of the fluid can be pushed or the fluid can be removed from the bottles regardless of whether the bottles are turned up or down.

Figure 6B:
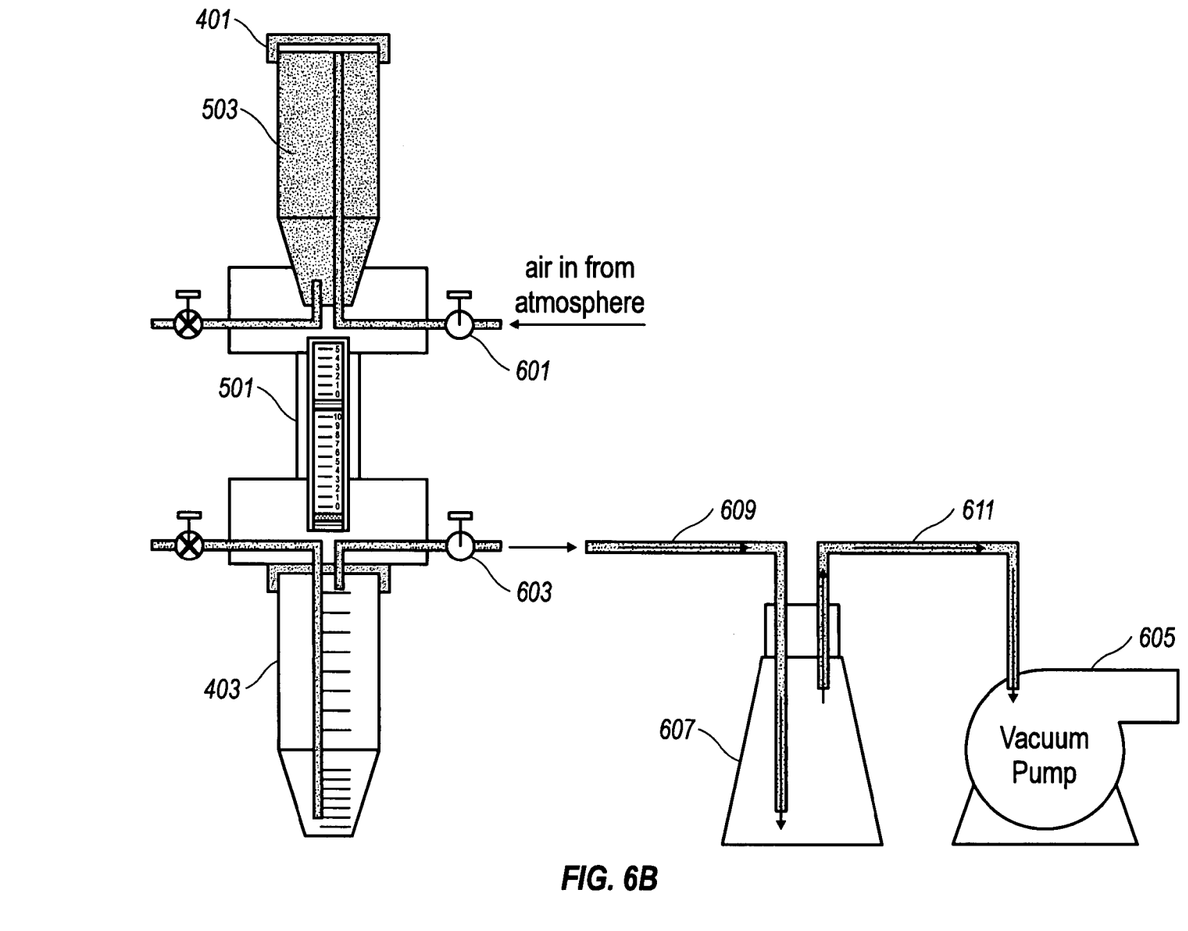

FIG. 6B shows an embodiment in which valve 603 is connected to a vacuum source 605 that can be used to pull fluid sample 503 through measurement column 501 and into flask 607 via ports 609 and 611.

Figure 6C:
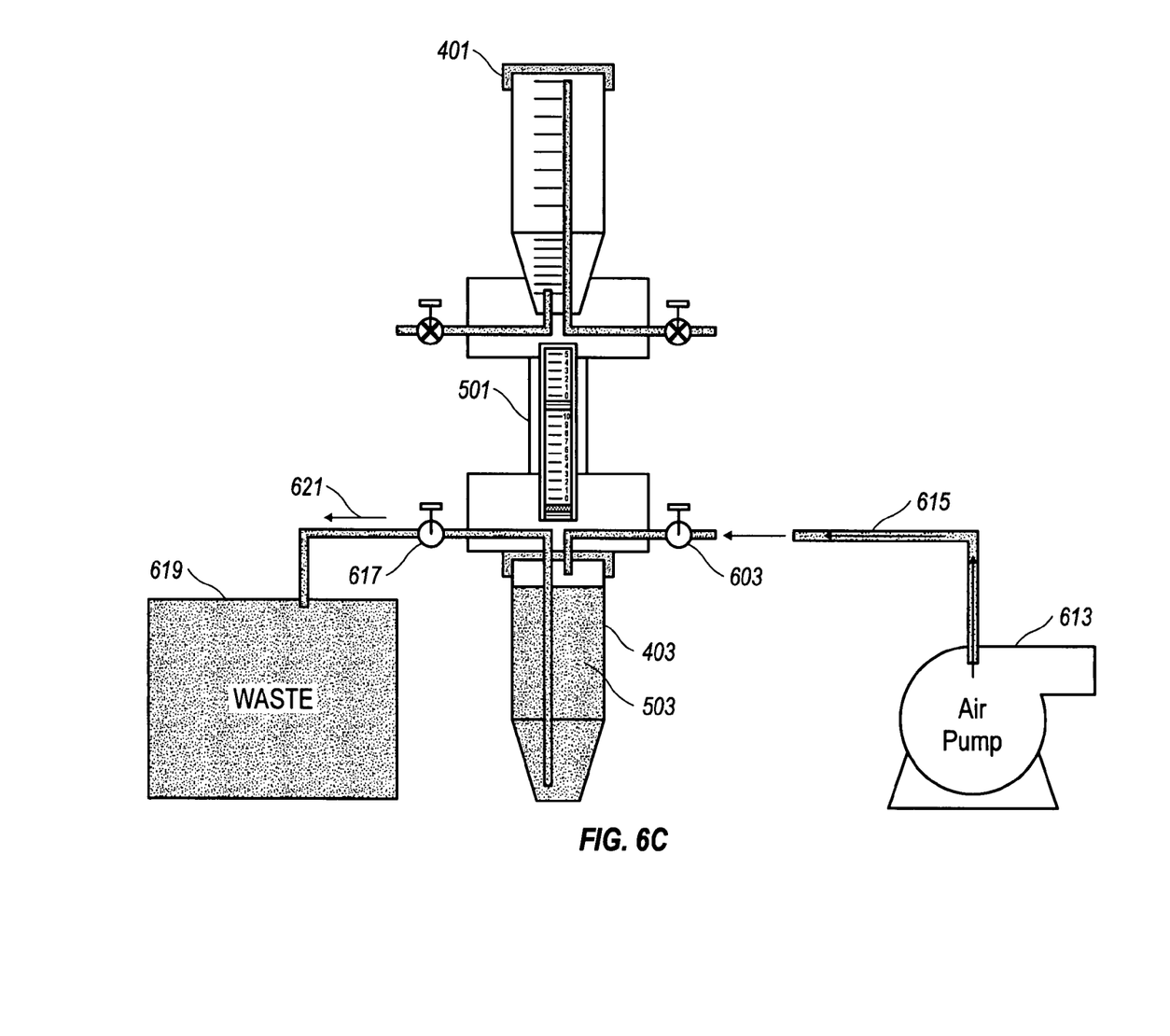

FIG. 6C shows an embodiment that uses pressure to remove fluid sample 503 to waste. In this particular embodiment, valve 603 delivers air pressure to the top of receiver bottle 403 via air pump 613 and port 615. Valve 617 is opened to allow fluid sample 503 to be blown directly into the main disposal tank 619 via port 621.

As with the previous embodiments, measurement column 501 is replaceable to avoid contamination of the next sample, as well as minimizes disposal.

Figure 7:
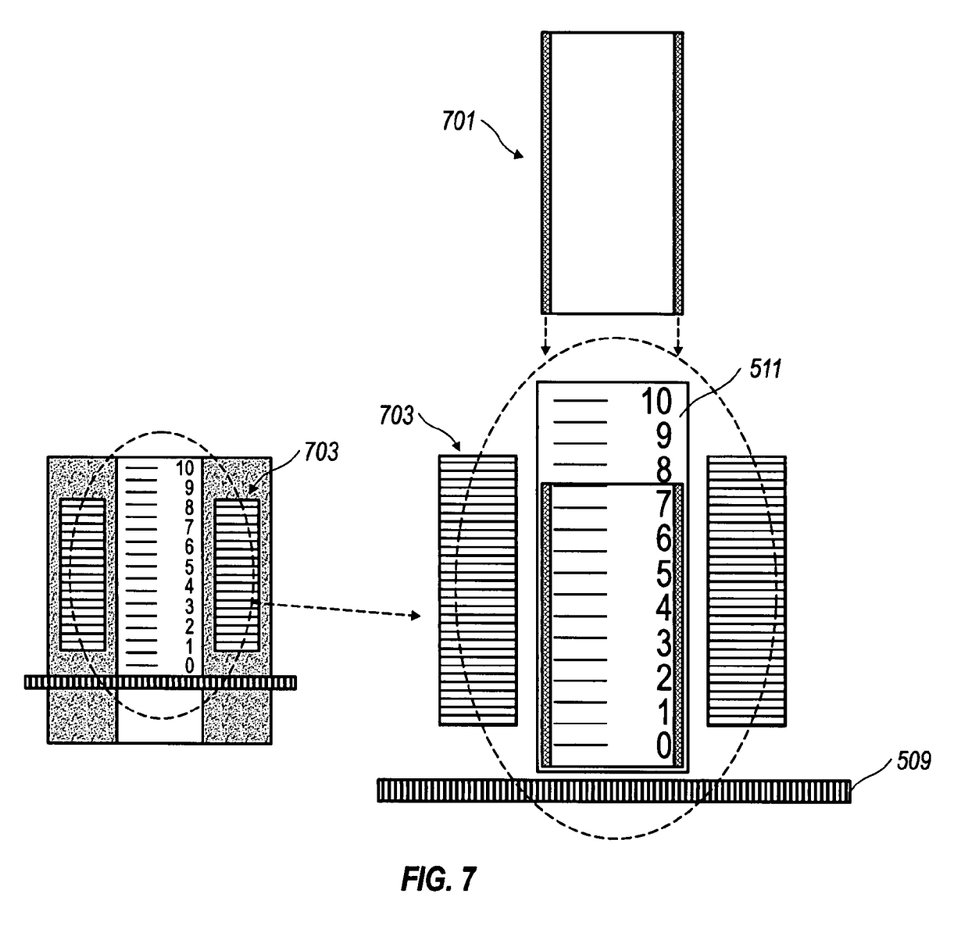
FIG. 7 depicts another general layout of the sediment measurement section.

FIG. 7 depicts another general layout of sediment measurement section 505. In this particular embodiment, a cylindrical, magnetic-coupled stirrer 701 is placed inside sight glass tube 511. Stirrer 701 forms a rotor to rotate the sample. This helps to prevent sediments from clogging filter 509. Magnetic coils 703 are pulsed in sequence to rotate the magnetic poles in the stirrer. Stirrer 701 can be, for example, a fired or pressed magnetic powder.

A very important advantage of the disclosed innovations is that they provide a measurement technique that is suitable for field use.

Another important advantage of the disclosed innovations is that they provide a measurement technique that is suitable for use by relatively untrained personnel. With sample conditions and additives standardized as described herein, a sampling technician can use the measurement unit without a thorough understanding of its operation because the measurements are so easily accomplished.

In one important class of embodiments, bottles and absorbents as described above are used for field assay at the point where a tanker is being loaded or unloaded. This very simple assay-at-lading technique provides simple verification of crude oil assay, and hence reduced commercial disputes.

In another class of embodiments, standardized bottles as described above can be used for field sampling (e.g. at sample collection tap valves at dockside). Thus, for example, a field auditor might fill a dozen labeled field bottles at various points in a pumping facility, and then return to the analyzer in his truck to obtain moisture and sediment analysis for each.

According to a disclosed class of innovative embodiments, there is provided: A system for measuring the fraction of water in a fluid stream comprising nonaqueous components, comprising: an apparatus which places a portion of the fluid stream into a measurement column and in contact with a premeasured amount of a high-uptake gelling agent within the measurement column, such that the gelling agent expands in correlation to the water content of the fluid stream; wherein the percentage of water in the fluid stream is determined by the volume of the expanded gelling agent.

According to a disclosed class of innovative embodiments, there is provided: A field-testing system for analysis of moisture and sediment content in non-aqueous samples, comprising: a field bottle for collecting a sample to be analyzed; a measurement column containing a high-uptake gelling agent which expands in correlation to the water content of the sample; and an apparatus which transfers the sample from the field bottle and into the measurement column, contacts the sample with the gelling agent within the measurement column, and collects the sample that passes through the measurement column into a receiver bottle; wherein the water content of the sample is determined by measuring the volume of the expanded gelling agent; and wherein the sediment content of the sample is estimated by reading its level from a graduated sight glass of a filter section.

According to a disclosed class of innovative embodiments, there is provided: A system for measuring the fraction of water in a fluid stream comprising nonaqueous components, comprising: at least one centrifuge tube with a fixed volume of the fluid stream and an adequate amount of a high-uptake gelling agent; wherein the centrifuge tube is centrifuged and the percentage of water in the fluid stream is determined by the volume of the expanded gelling agent.

DEFINITIONS

Following are short definitions of the usual meanings of some of the technical terms which are used in the present application. (However, those of ordinary skill will recognize whether the context requires a different meaning.) Additional definitions can be found in the standard technical dictionaries and journals.

The term "high-uptake gelling agent" is used to describe any material or substance that is able to absorb at least 30 times its own mass of water.

MODIFICATIONS AND VARIATIONS

As will be recognized by those skilled in the art, the innovative concepts described in the present application can be modified and varied over a tremendous range of applications, and accordingly the scope of patented subject matter is not limited by any of the specific exemplary teachings given.

One advantage of the present invention includes a decrease in error for determining, for example, the water and sediment content of a crude oil sample. Human operators can damage equipment, ruin calibration or settings, and influence the apparatus in other ways when handling sensitive testing equipment in the field. In the present invention, pre-packaged amounts of a high-uptake gelling agent and the general hardiness and simplicity of the testing process and apparatus reduce human actions that must be taken in order to obtain an estimate of the water and sediment content in a sample. Further, a field test kit of the present innovations requires no trained technician for operation, and can be safely and effectively used by unskilled operators.

In one embodiment, the present invention allows testing of, for example, crude oil as it is in transport or exchanging possession, ownership, crossing political or legal boundaries, containers, etc. For example, crude oil unloaded from a ship to a new political boundary often requires an assessment of the actual amount of oil, which in turn requires an assessment of the amount of water in the offloaded fluid. The innovations of the present application provide an easy and effective means of providing the necessary information.

The measurement column may be sealed for convenient disposal of hazardous solvents. This would help in the transportation of the sample titer to the hazardous waste disposal through the laboratory ambient.

In a further alternative embodiment, the measurement column can be prefilled with the high-uptake gelling agent and then foiled-sealed. Foil-sealing the prefilled measurement column protects the high-uptake gelling agent from moisture contamination before the sample is introduced.

None of the description in the present application should be read as implying that any particular element, step, or function is an essential element which must be included in the claim scope: THE SCOPE OF PATENTED SUBJECT MATTER IS DEFINED ONLY BY THE ALLOWED CLAIMS. Moreover, none of these claims are intended to invoke paragraph six of 35 USC section 112 unless the exact words "means for" are followed by a participle.

The claims as filed are intended to be as comprehensive as possible, and NO subject matter is intentionally relinquished, dedicated, or abandoned.

What is claimed is:

1. A system for measuring the fraction of water in a fluid stream comprising nonaqueous components, comprising:
    an apparatus which passes a known quantity of the fluid stream through a measurement column, said column comprising:
        (i) an inlet opening at one end of said column;
        (ii) an outlet opening at the other end of said column;
        (iii) a graduated scale;
        (iv) a premeasured excess amount of a loose particulated high-uptake gelling agent within the measurement column, such that the gelling agent expands in correlation to the water content of the fluid stream; and
        (v) a filter at said outlet opening of said other end of column;
    wherein the percentage of water in the fluid stream is determined by the volume of the expanded gelling agent.

2. The system of claim 1, wherein the system uses suction created by a vacuum applied to said outlet opening at said other end of said column to thereby draw the fluid stream through said first opening and across the gelling agent, and then out of said column through said second opening.

3. The system of claim 1, wherein the measurement column also contains an inert solid to thereby form occlusions to facilitate the movement of the fluid stream across the gelling agent.

4. The system of claim 1, wherein the system includes a pre-filter section having a sight glass with graduations to determine the sediment content of the fluid stream; wherein said fluid passes through said pre-filter section prior to contact with said gelling agent.

5. The system of claim 1, wherein the system also comprises a stirrer for stirring the fluid stream as it is placed into the measurement column.

6. The system of claim 1, wherein the system includes a marker which allows the volume of the expanded gelling agent to be more discernible.

7. The system of claim 6, wherein the marker is selected from the group consisting of anhydrous salts, florescent dyes, and hydrophilic membranes.

8. The system of claim 1, wherein the gelling agent is selected from the group consisting of a crosslinked polymer, an acrylic-based polymer, polyacrylic acid, and mixtures thereof.

9. The system of claim 1, wherein the gelling agent is selected from the group consisting of sodium polyacrylate, polyethylene oxide, a maleic anhydride/vinyl ether copolymer, poly(methacrylic acid), a carboxyalkyl starch, and mixtures thereof.

10. The system of claim 1, wherein the gelling agent has a known ratio of total expanded volume to volume of moisture absorbed.

11. The system of claim 1, wherein said gelling agent is dry.

12. The system of claim 1, wherein said gelling agent is granular.

13. A field-testing system for analysis of moisture and sediment content in non-aqueous samples, comprising:
- a field bottle for collecting a sample to be analyzed;
- a measurement column containing a loose particulated high-uptake gelling agent which expands in correlation to the water content of the sample; and
- an apparatus which
  - transfers the sample from the field bottle, through an inlet opening at one end of the measurement column, and then through a pre-filter section, and then into the measurement column,
  - contacts the sample with the gelling agent within the measurement column, and
  - collects the sample that passes through the measurement column, and then through an outlet opening at the other end of the measurement column and into a receiver bottle;
- wherein the water content of the sample is determined by reading a graduated scale on said column thereby measuring the volume of the expanded gelling agent; and
- wherein the sediment content of the sample is estimated by reading its volume from a graduated sight glass of said pre-filter section.

14. The system of claim 13, wherein the system also comprises a stirrer for stirring the sample as it is transferred to the measurement column.

15. The system of claim 13, wherein the system uses suction created by a vacuum applied to a second opening at said other end of said column to thereby draw the fluid stream through said inlet opening and across the gelling agent, and then out of said column through said outlet opening.

16. The system of claim 13, wherein the measurement column also contains an inert solid to thereby form occlusions to facilitate the movement of the fluid stream across the gelling agent.

17. The system of claim 13, wherein the measurement column includes a marker which allows the volume of the expanded gelling agent to be more discernible.

18. The system of claim 17, wherein the marker is selected from the group consisting of anhydrous salts, florescent dyes, and hydrophilic membranes.

19. The system of claim 13, wherein the gelling agent is selected from the group consisting of a crosslinked polymer, an acrylic-based polymer, polyacrylic acid, and mixtures thereof.

20. The system of claim 13, wherein the gelling agent is selected from the group consisting of sodium polyacrylate, polyethylene oxide, a maleic anhydride/vinyl ether copolymer, poly(methacrylic acid), a carboxyalkyl starch, and mixtures thereof.

21. The system of claim 13, wherein the gelling agent has a known ratio of total expanded volume to volume of moisture absorbed.

22. The system of claim 13, wherein said gelling agent is dry.

23. The system of claim 13, wherein said gelling agent is granular.

24. A system for measuring the fraction of water in a fluid stream comprising nonaqueous components, comprising:
- an apparatus which places a known quantity of the fluid stream into a measurement column and in contact with a premeasured amount of a high-uptake gelling agent within the measurement column, such that the gelling agent expands in correlation to the water content of the fluid stream;
- wherein the percentage of water in the fluid stream is determined by the volume of the expanded gelling agent
- further comprising a plunger assembly which filters out the absorbent gel from a fluid sample.

* * * * *